United States Patent
Chen et al.

(10) Patent No.: US 11,254,946 B2
(45) Date of Patent: Feb. 22, 2022

(54) METHOD FOR INCREASING LYCOPENE CONTENT IN TOMATO FRUIT

(71) Applicant: Zhejiang Normal University, Zhejiang (CN)

(72) Inventors: Xifeng Chen, Jinhua (CN); Bojun Ma, Jinhua (CN); Shunli Chen, Jinhua (CN); Youyi Wu, Jinhua (CN); Yaping Liu, Jinhua (CN)

(73) Assignee: Zhejiang Normal University, Jinhua (CN)

( * ) Notice: Subject to any disclaimer, the term of this patent is extended or adjusted under 35 U.S.C. 154(b) by 0 days.

(21) Appl. No.: 16/881,003

(22) Filed: May 22, 2020

(65) Prior Publication Data

US 2020/0291412 A1    Sep. 17, 2020

Related U.S. Application Data

(63) Continuation-in-part of application No. PCT/CN2019/089016, filed on May 29, 2019.

(30) Foreign Application Priority Data

Dec. 24, 2018 (CN) .......................... 201811580111.9

(51) Int. Cl.
  *C12N 15/82* (2006.01)
  *A01H 6/82* (2018.01)

(52) U.S. Cl.
  CPC .......... *C12N 15/825* (2013.01); *A01H 6/825* (2018.05)

(58) Field of Classification Search
  CPC .................................. C12N 15/82; A01H 6/825
  See application file for complete search history.

(56) References Cited

PUBLICATIONS

Li et al. (Linkage between the I-3 gene for resistance to Fusarium wilt race 3 and increased sensitivity to bacterial spot in tomato. Theor Appl Genet 131:145-155, published online Oct. 2017) (Year: 2017).*
NCBI (XM_004246695, publish, applicant admitted) (Year: 2018).*
As support to Li et al., Catanzariti et al. (The tomato I-3 gene: a novel gene for resistance to Fusarium wilt Disease. New Phytologist 207: 106-118, 2015) (Year: 2015).*
Prihatna et al (A Novel Tomato Fusarium Wilt Tolerance Gene. Frontiers in Microbiology. 1-11, Jun. 2018) (Year: 2018).*
Ling et al. (Improving the efficiency of precise genome editing with site-specific Cas9-oligonucleotide conjugates. Sci. Adv. 1-8, 2020) (Year: 2020).*
Poonam Chaudhary et al., Bioactivities of Phytochemicals Present in Tomato, Journal of Food Science & Technology, 2018, pp. 2833-2849, vol. 55.
Seisuke Kimura et al., Tomato Transformation, Cold Spring Harbor Protocols, 2008, pp. 1-3, vol. 3, Issue 11.
Kenneth J. Livak et al., Analysis of Relative Gene Expression Data Using Real-Time Quantitative PCR and the 2(-ΔΔCT) Method, Methods, 2001, pp. 402-408, vol. 25.
Jamal Javanmardi et al., Variation of Lycopene, Antioxidant Activity, Total Soluble Solids and Weight Loss of Tomato During Postharvest Storage, Postharvest Biology and Technology, 2006, pp. 151-155, vol. 41.
Sabel Marti'nez-Valverde et al., Phenolic Compounds, Lycopene and Antioxidant Activity in Commercial Varieties of Tomato (*Lycopersicum esculentum*), Journal of the Science of Food and Agriculture, 2002, pp. 323-330, vol. 82.
F Ann Ran et al., Genome Engineering Using the CRISPR-Cas9 System, Nature Protocols, 2013, pp. 2281-2308, vol. 8.
Ophir Shalem et al., Genome-Scale CRISPR-Cas9 Knockout Screening in Human Cells, Science, 2014, pp. 84-87, vol. 343.
Ramachandran Srinivasan et al., Accumulation of Phytoene, a Colorless Carotenoid by Inhibition of Phytoene Desaturase (PDS) Gene in Dunaliella Salina V-101, Bioresource Technology, 2017, pp. 311-318, vol. 242.
Predicted: Solanum Lycopersicum Uncharacterized LOC101246275, mRNA GenBank: XM_004246695.4, Aug. 3, 2018.

* cited by examiner

*Primary Examiner* — Bratislav Stankovic
*Assistant Examiner* — Wayne Zhong

(57) ABSTRACT

The present disclosure provides a method for increasing lycopene content in a tomato fruit, including knocking out the gene LIE1 of SEQ ID No 1. The disclosure also provides a method for knocking out gene LIE1 in tomato. The method of the disclosure is effective for increasing the content of lycopene in tomato fruits. Finally, the disclosure provides a transgenic tomato plant with knockout of gene LIE1.

4 Claims, 2 Drawing Sheets
(1 of 2 Drawing Sheet(s) Filed in Color)

Specification includes a Sequence Listing.

METHOD FOR INCREASING LYCOPENE CONTENT IN TOMATO FRUIT

CROSS REFERENCE TO RELATED APPLICATION

The present application is a continuation-in-part application of PCT application No. PCT/CN2019/089016 filed on May 29, 2019, which claims the benefit of Chinese Patent Application No. 201811580111.9 filed on Dec. 24, 2018. The contents of the above applications are incorporated herein by reference in their entirety.

REFERENCE TO SEQUENCE LISTING

The substitute sequence listing is submitted to replace the previously submitted sequence listing as an ASCII formatted text filed via EFS-Web, with a file name of "Substitute_Sequence_Listing_ZZZHCH-19006-USPT.txt", a creation date of Oct. 20, 2020, and a size of 5,263 bytes. The substitute sequence Listing filed via EFS-Web is part of the specification and is incorporated in its entirety by reference herein.

FIELD

The disclosure relates to a method for increasing lycopene content in tomato fruit using CRIPSR/Cas9 gene-editing technology, belonging to the field of crop molecular breeding.

BACKGROUND

Tomato is an important vegetable and fruit, and its ripe fruit contains a lot of lycopene. Lycopene, a kind of carotenoid, is one of the strongest antioxidants found in nature, whose ability of scavenging free radicals is far superior to the other carotenoids and vitamin E. Therefore, lycopene has various functions in anti-aging, anti-cancer, inhibition of digestive tract and cardiovascular diseases (Chaudhary, et al. 2018). It has great values in researches and application to find the genes which can effectively improve lycopene content in tomato fruits.

The RNA-guided Cas9 nuclease from the microbial clustered regularly interspaced short palindromic repeats (CRISPR) adaptive immune system can be used to facilitate efficient genome engineering in eukaryotic cells by simply specifying a 20-nt targeting sequence within its guide RNA (Ran et al. 2013). The CRISPR/Cas9 provides an effective means of introducing targeted loss-of function mutations at specific sites in the genome. Cas9 can be programmed to induce DNA double strand breaks at specific genomic loci through a synthetic single guide RNA (sgRNA), which when targeted to coding regions of genes can create frame shift mutations that result in a loss-of-function allele (Shalem et al. 2014). Therefore, the CRISPR/Cas9 technology was wildly used to knockout target genes in plants and animals.

SUMMARY

In the present application, the technical problem to be solved is how to effectively increase the content of lycopene in tomato fruits.

In order to solve the technical problem above, the present disclosure provides a tomato gene LIE1 (Lycopene Increasing Effectively 1): *Solanum lycopersicum* uncharacterized LOC101246275, mRNA GenBank accession is XM_004246695.4, and its nucleotide of codon sequence is shown as SEQ ID NO: 1.

The disclosure also provides a method for increasing lycopene content in a tomato fruit, including knocking out the gene Lycopene Increasing Effectively 1 (LIE1) of SEQ ID NO. 1 in the tomato fruit.

The disclosure also provides a method for knocking out gene LIE1 in tomato, including the following steps:
1) obtaining a gene specific targeting sgRNA of the following sequence:

```
sgRNA-1:
                              (SEQ ID NO. 4)
5'-TCTTCTCAATACATCCACA-3';
or sgRNA-2:
                              (SEQ ID NO. 5)
'5'-GGCTGAATATTTGCATGTT-3';
```

2) constructing a CRISPR/Cas9 vector using the sgRNA sequence obtained in step 1); and
3) transforming the vector obtained in step 2) into a tomato to obtain a transgenic tomato plant in which the gene LIE1 is knocked out.

The disclosure further provides a transgenic tomato plant, in which the gene Lycopene Increasing Effectively 1 (LIE1) is knocked out.

In a preferred embodiment, the gene LIE1 is knocked out through introducing the following frameshift mutations:
a) insertion of a base C in the first exon of the gene LIE1, resulting a LIE1 mutant of SEQ ID NO: 2; and/or
b) deletion of a base T in the second exon of the gene LIE1, resulting a LIE1 mutant of SEQ ID NO: 3.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The specific embodiments of the present disclosure are described in further detail below with reference to the accompanying drawings.

Figure 3:
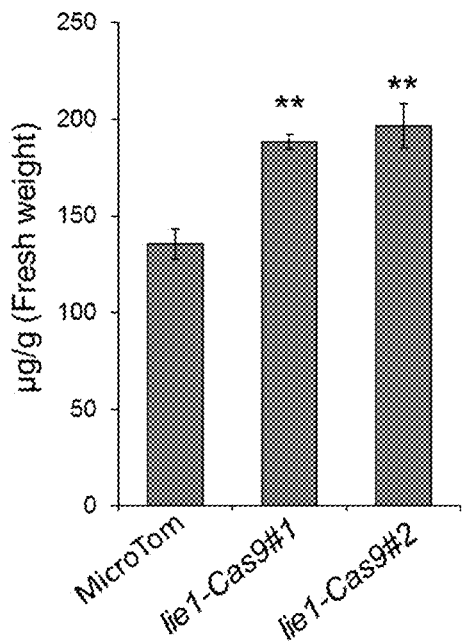
FIG. 3 shows the lycopene content in mature fruits of tomato.
Figure 4:
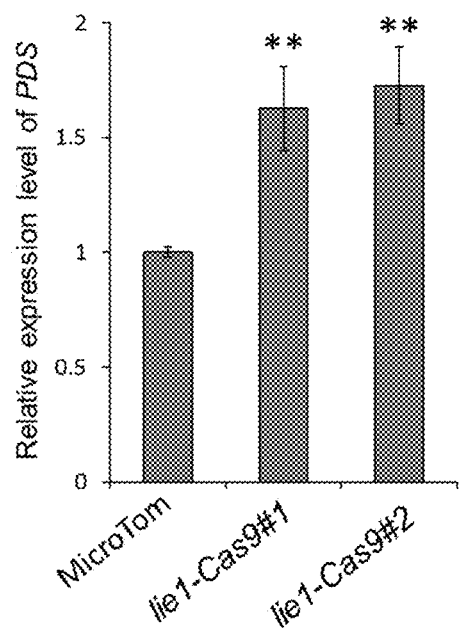
FIG. 4 shows the expression level of gene phytoene desaturase (PDS) in pre-mature fruits of tomato.

For all figures, MicroTom refers to the wild-type control tomato; lie1-Cas9#1 and lie1-Cas9#2 refer to the two transgenic lines with gene LIE1 knockout by CRISPR/Cas9. The values in FIGS. 3 and 4 are mean±standard deviation, ** indicates an extremely significant difference (P<0.01) by the t-test in between the transgenic line lie1-Cas9#1 (or lie1-Cas9#2) and the wild-type control MicroTom.

DETAILED DESCRIPTION OF THE EMBODIMENTS

Figure 1:
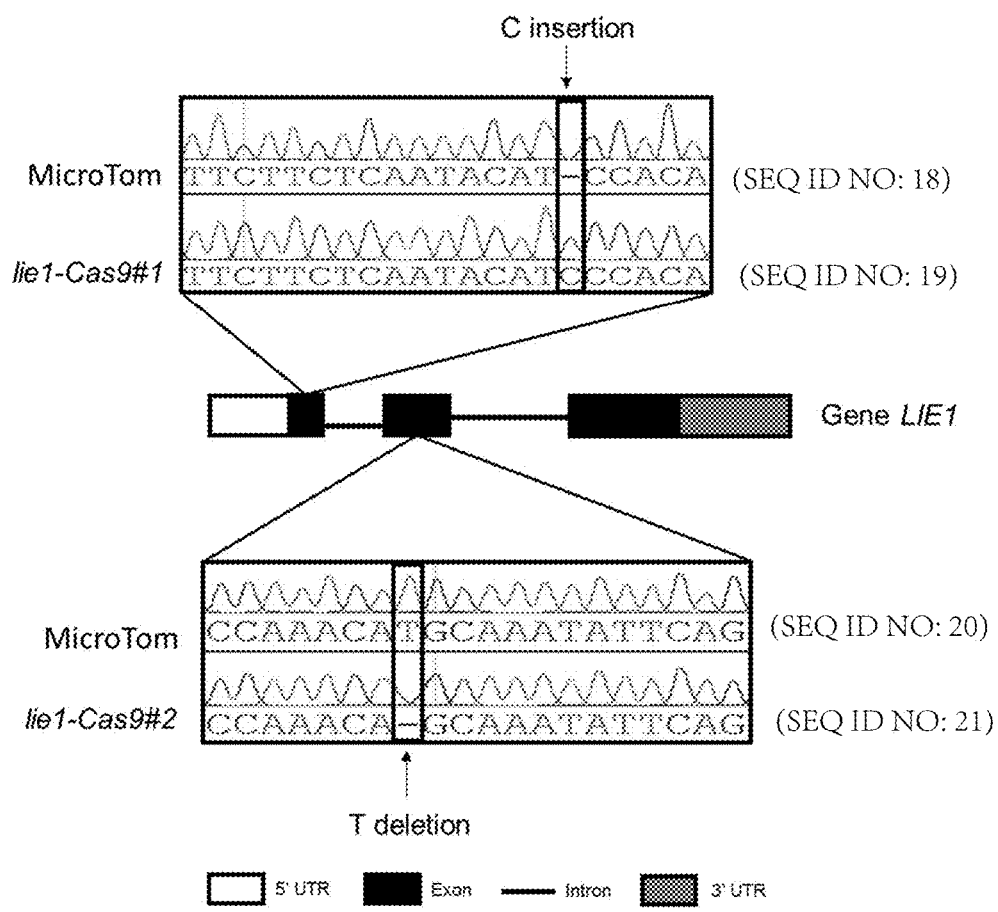
FIG. 1 shows the sequence of the CRISPR/Cas9 targeting sites in gene LIE1.

By using the CRISPR/Cas9 technique, two sgRNAs specific targeting gene LIE1 was designed and transformed into a wild-type tomato MicroTom to knock out the gene LIE1, and two different frameshift-mutation transgenic lines of gene LIE1 were obtained, which named as line lie1-Cas9#1 and line lie1-Cas9#2 (FIG. 1). Compared with the sequence of wild-type control MicroTom, a base C insertion happened in the first exon of gene LIE1 in the line lie1-Cas9#1, and a base T deletion happened in the second exon of gene LIE1 in the line lie1-Cas9#2 (FIG. 1), both of which resulted in frameshift mutation and loss function of gene LIE1, also known as knockout of gene LIE1. The sequence of gene LIE1 in the line lie1-Cas9#1 is described as SEQ ID NO: 2, and the sequence of gene LIE1 in the line lie1-Cas9#2 is described as SEQ ID NO: 3.

Example

Step 1. Construction of CRISPR/Cas9 Vector for Knocking Out Gene LIE1

According to the coding sequence (CDS) of gene LIE1 (SEQ ID NO: 1), two CRISPR/Cas9 targeting sgRNAs were designed by CRISPR Design program (http://crispr.mit.edu/), and the sequences are sgRNA-1: 5'-TCTTCT-CAATACATCCACA-3' (SEQ ID NO: 4), sgRNA-2: 5'-GGCTGAATATTTGCATGTT-3' (SEQ ID NO: 5). A construction kit of the CRISPR/Cas9 vector (Biogle, Cat #BGK01) were used by the steps:

(1) Synthesis of oligos. According to the sequence of sgRNA, the oligo pairs were artificially synthesized by company:

For the sgRNA-1, the sequences of oligo pair were

```
UP:
                                        (SEQ ID NO: 6)
5'-TGATTGTCTTCTCAATACATCCACA-3'

Low:
                                        (SEQ ID NO: 7)
5'-AAACTGTGGATGTATTGAGAAGACA-3'
```

For the sgRNA-2, the sequences of oligo pair were

```
UP:
                                        (SEQ ID NO: 8)
5'-TGATTGGGCTGAATATTTGCATGTT-3'

Low:
                                        (SEQ ID NO: 9)
5'-AAACAACATGCAAATATTCAGCCCA-3'
```

Note: the bases underlined were used for matching with the vector of CRISPR/Cas9.

(2) Preparation of oligo dimer. Each oligo pair synthesized were dissolved in water to the concentration of 10 μM, and 1 μl UP oligo, 1 μl Low oligo and 18 μl Buffer were mixed. The mixture was incubated on 95° C. for 3 minutes, and then slowly reducing to 20° C.

(3) Construction of Oligo dimer into CRISPR/Cas9 vector. One μl oligo dimer, 2 μl linearized CRISPR/Cas9 Vector, 1 μl Enzyme Mix and 6 μl ddH$_2$O were mixed on ice and room temperature (about 20° C.) for 1 hour.

(4) Transformation of CRISPR/Cas9 Vector into *E. coli*. Five μl reaction solution above was mixed with the competent cells of *E. coli*, and incubated on ice for 30 minutes and then on 42° C. for 1 minute, and immediately transferred on ice for 2 minutes. The reaction solution was added into 500 μl LB liquid medium, and incubated at 37° C. with shaking 200 rpm for 1 hour. A proper amount of bacterial solution was applied on the LB plate containing kanamycin, and incubated at 37° C. overnight.

(5) PCR identification of colonies. Each monoclonal colonies were picked respectively into 10 μl ddH$_2$O by tips and mixed. GoTaq® Green Master Mix (Promega, Cat. M7121) was used for PCR. Total 25 μl volume of reaction solution was prepared with 12.5 μl Go Taq® Green Master Mix (2×), 0.5 μl forward primer (10 μM), 0.5 μl reverse primer (10 μM), 1 μl bacterial fluid of monoclonal colony and 10.5 μl ddH$_2$O. The primer pair used for PCR were forward: 5'-TCCCAGTCACGACGTTGTAA-3' (SEQ ID NO: 10) and reverse: 5'-TTCAAGTTGA-TAACGGACTAGC-3' (SEQ ID NO: 11). The PCR program was followed as: 94° C. for 5 min; 35 cycles of 94° C. for 30 sec, 55° C. for 30 sec and 72° C. for 45 sec; 72° C. for 5 min. The PCR products was electrophoresed on a 1% agarose gel for 30 min and stained by ethidium bromide (EB). The PCR products with the correct band size (410 bp) were sequenced using the primer of 5'-TCCCAGTCACGACGTTGTAA-3' (SEQ ID NO: 10) for final verification.

Step 2. Genetic Transformation of Tomato by CRISPR/Cas9 Vector Constructed

The two CRISPR/Cas9 vectors constructed were respectively transformed into the wild-type tomato MicroTom by the method described by Kimura and Sinha (2008) with the following steps:

(1) Surface-sterilize tomato seeds by immersing them in 70% ethanol and swirling them for 2 min at room temperature.

(2) Immerse the seeds in 50% bleach for 15-20 min at room temperature with gentle swirling.

(3) Wash off the bleach completely by rinsing the seeds five to 10 times with H$_2$O under a sterile hood.

(4) Add 5 mL of H$_2$O to the seeds. Pour the seeds into a Magenta box containing germination medium for tomato. Place the cover on the Magenta box and put it in a growth chamber (26° C., 16-h photoperiod).

(5) Use sterilized forceps and scissors to harvest a cotyledon from an 8- to 10-d-old plant and place it in a Petri dish. Keep the cotyledons moist by adding ~20 mL of MSO liquid medium to the dish. (6) Cut the tip and base of each cotyledon with a razor blade. Wound them with one to three shallow transverse cuts across the main vein on the adaxial side to facilitate *Agrobacterium* infection. Place the explants onto a Petri dish containing 20 mL of temporary medium.

(7) Streak the *Agrobacterium* onto an LB medium for tomato plate using an inoculating loop and incubate the plate at 28° C. until colonies form.

(8) Inoculate 10 mL of liquid LB medium for tomato with a single *Agrobacterium* colony in a culture tube. Incubate the culture with shaking overnight at 28° C. and then measure the OD$_{600}$ of the culture using a spectrophotometer. The optimum OD$_{600}$ is 0.6-0.7.

(9) Harvest the *Agrobacterium* by centrifugation at 3000 g for 15 min at room temperature and resuspend the cells with an appropriate amount of MSO liquid medium to make the OD$_{600}$ of the suspension ~0.5.

(10) Pour ~5 mL of the *Agrobacterium* suspension (from Step 9) onto the temporary medium with the explants (from Step 6).

(11) Incubate the explants on the temporary medium for 2 h at room temperature.

(12) Remove excess *Agrobacterium* suspension with a transfer pipette. Seal the plate with surgical tape.

(13) Cocultivate explants in the growth chamber (26° C., 16-h photoperiod) for 48 h.

(14) Transfer the explants onto a Petri dish containing selection medium for tomato. (Keep the adaxial side up.) Seal the dish with surgical tape.

(15) Keep the explants in the growth chamber (26° C., 16-h photoperiod) until a callus forms. Transfer the explants to new selection medium for tomato every 2 weeks or when *Agrobacterium* is growing in the medium.

(16) When shoots get to ~2-4 cm, excise them from the explants and transfer them to a Magenta box that contains rooting medium.

(17) Keep the Magenta box in a growth chamber (26° C., 16-h photoperiod).

(18) When the shoots are ~5 cm and the roots are established, take the transformants out of the Magenta box and gently wash off the agar.

(19) Transplant the transformants to a pot with wet soil.

(20) Place a clear plastic cover on the pot to keep moisture in and put it in the growth chamber (26° C., 16-h photoperiod) for ~1 week.

(21) After 1 week, transfer the pot to the greenhouse (25° C., 16-h photoperiod) and let the plants grow.

Step 3. Sequencing of CRISPR/Cas9 Target Sites in the Genome of Transgenic Tomato Plants (1) Extraction of genomic DNA. For each plants of wild-type control MicroTom, and the tow transgenic lines, 0.1 g leaves were ground with liquid nitrogen by mortar, and transferred into a 1.5 ml tube mixed with 600 µl extraction solution (0.1 M Tris-Cl pH 8.0, 500 mM NaCl, 1.5% SDS) and incubated at 65° C. for 60 min. 200 µl 5M KAC was added and mixed by vortex, and then incubated in an ice bath for 10 min. 500 µl of chloroform was added and mixed by vortex, and then centrifuged at 10000 rpm for 5 min. The supernatant was transferred into a new tube, and 500 µl isopropanol was added and mixed by vortex. After centrifuge at 12000 rpm for 3 min, the supernatant was discarded. The precipitate was washed by 75% ethanol, and the supernatant was discarded after centrifuge at 12,000 rpm for 3 min. The DNA was dissolved to 30 µl of ddH$_2$O and these samples were used for PCR in next step.

(2) PCR amplification and gel electrophoresis. GoTaq® Green Master Mix (Promega, Cat. M7121) was used for PCR with the genomic DNA samples. Total 25 µl volume of reaction solution was prepared with 12.5 µl Go Taq® Green Master Mix (2×), 0.5 µl forward primer (10 µM), 0.5 µl reverse primer (10 µM), 1 µl genomic DNA and 10.5 ddH$_2$O. The primer pair used for PCR were forward: 5'-CAATTTTATTTTGAACGGAG-3' (SEQ ID NO: 12) and reverse: 5'-TTTACCTGTGGAAGTGAT-3' (SEQ ID NO: 13). The PCR program was followed as: 94° C. for 5 min; 35 cycles of 94° C. for 30 sec, 55° C. for 30 sec and 72° C. for 45 sec; 72° C. for 10 min. The PCR products was electrophoresed on a 1% agarose gel for 30 min and stained by ethidium bromide (EB). The PCR products showing the correct size of bands (about 620 bp) were used for sequencing in next step.

(3) Sequencing of PCR products and sequence analysis. The PCR products were sent to biotechnology companies for sequencing by the primer 5'-CAATTTTATTTTGAACG-GAG-3' (SEQ ID NO: 12). The result sequences were analyzed by the software of SeqMan to compare the sequence difference of gene LIE1 between the wild-type control MicroTom and the two transgenic lines in the target sites edited by CRISPR/Cas9.

Step 4. Assay of Lycopene Content in Fruit of the Transgenic Tomato Plants

After the stage of fruit mature, 3 plants of the wild-type control MicroTom and the two transgenic lines were randomly selected respectively, and then 3 fruits were taken from each plant for analysis Lycopene content following steps:

(1) Extraction of Lycopene. For each fruit, 0.2 g of tissue was ground into powder with liquid nitrogen, and 8 mL extraction solution of hexane:ethanol:acetone (2:1:1, V:V:V) was added, and incubated at room temperature shaking 100 rpm overnight.

(2) Measurement of Lycopene content. The absorbance of the organic phase at 503 nm was used according to the methods described by (Martínez-Valverde, et al., 2002; Javanmardi, et al, 2006). One mL H$_2$O was added into the solution and mixed by vortex, and the solvent layer (upper layer) was measured using spectrophotometer at 503 nm absorbance normalized by hexane. Each measurement was done for three repeats. The lycopene content was calculated by the following formula:

Lycopene (µg/g)=(x/y)×A503×3.12

Note: 'x' stands for the amount of hexane (ml), 'y' stands for the weight (g) of fruit tissue, 'A503' stands for the measurement value at 503 nm absorbance, and '3.12' is the extinction coefficient.

A significant difference of measurement between the wild-type control MicroTom and the two transgenic lines was analyzed by t-test.

Step 5. Expression Analysis of Gene PDS (1) RNA extraction. Before the stage of fruit mature, 3 plants of wild-type control MicroTom and the two transgenic lines were randomly selected respectively, and then 3 fruits were taken from each plant. Total RNA from each fruit were extracted using the RNeasy Plant Mini Kit (Qiagen, Cat. 74903) according to the manufacturer's instructions.

(2) Reverse transcription of RNA. The total RNA samples were reverse-transcribed respectively into cDNA using the Prime Script™ RT reagent Kit with gDNA Eraser (Takara, Cat. RR047Q) according to the manufacturer's instructions.

(3) Real-time PCR. TB Green™ Premix Ex Taq™ (Takara, Cat. RR420L) kit was used for real-time PCR of the PDS gene from the cDNA samples above. Total 25 µl volume of reaction solution was prepared with 12.5 µl TB Green Premix Ex Taq (2×), 0.5 µl forward primer (10 µM), 0.5 µl reverse primer (10 µM), 2 µl cDNA and 9.5 µl ddH$_2$O. Primer pair of gene PDS were used as forward: 5'-ACGAAACAGAAATACTTGGC-3' (SEQ ID NO: 14). and reverse: 5'-CTTCCGACAACTTCTTTTGG-3' (SEQ ID NO: 15). Gene Actin was used for normalization with the primer pair as forward: 5'-CAGCAGATGTG-GATCTCAAA-3' (SEQ ID NO: 16) and reverse: 5'-CTGTGGACAATGGAAGGAC-3' (SEQ ID NO: 17). Real-time PCR was performed by Applied Biosystems 7500Fast Dx Real-Time PCR Instrument suing the program of 95° C. for 30 sec, and then 40 cycles of 95° C. for 5 sec and 60° C. for 30 sec. The raw data from real-time PCR were analyzed by the $2^{-\Delta\Delta Ct}$ method (Livak and Schmittgen, 2001).

Figure 2:
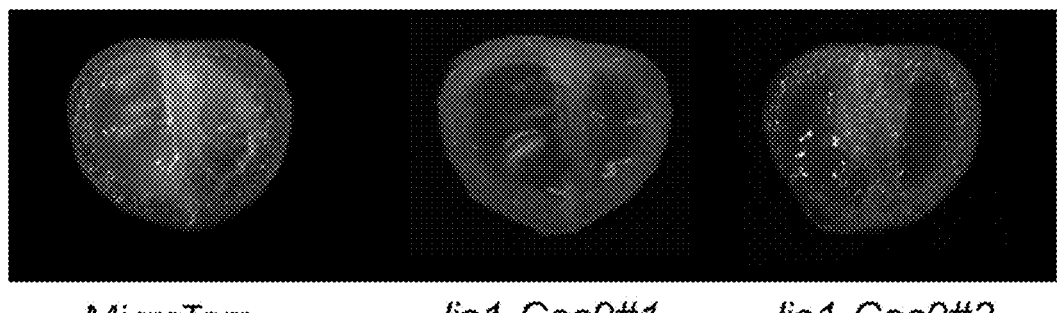
FIG. 2 shows the color comparison inside mature fruits of tomato.

For the mature fruits of tomato of the line lie1-Cas9#1 and line lie1-Cas9#2, the color is redder (FIG. 2) and the lycopene contents of are significantly higher than the wild-type control MicroTom (FIG. 3). Meanwhile, the gene expression of phytoene desaturase (PDS), which encodes a key enzyme for lycopene biosynthesis (Srinivasan, et al. 2017), was analyzed in the tomato immature fruits by qPCR.

Compared with the wild-type control MicroTom, the expression level of gene PDS was significantly increased in the line lie1-Cas9#1 and line lie1-Cas9#2 (FIG. 4). These results indicated that gene LIE1 negatively regulates the expression of PDS gene in tomato, and knocking out gene LIE1 in tomato can increase the expression of PDS gene, thereby promoting the biosynthesis of lycopene in tomato fruits. These results indicated that gene LIE1 is valuable in breeding application of tomato.

Finally, it is important to note that the above description is only specific embodiments of the present disclosure. Obviously, the disclosure is not limited to the above embodiments, but can also have a lot of deformation. All the deformation that the general technical personnel in this field can directly derive or associate with the contents disclosed in this field should be considered as the scope of protection of the disclosure.

REFERENCES

[1] Chaudhary P, Sharma A, Singh B, et al. Bioactivities of phytochemicals present in tomato. Journal of Food Science & Technology, 2018, 55: 2833-2849.
[2] Kimura S and Sinha N. Tomato Transformation. Cold Spring Harbor Protocols, 2008, 3:1-3.
[3] Livak K J and Schmittgen T D. Analysis of relative gene expression data using real-time quantitative PCR and the $2^{(-\Delta\Delta Ct)}$ Method. Methods, 2001, 25:402-408.
[4] Javanmardi J, Kubota C. Variation of lycopene, antioxidant activity, total soluble solids and weight loss of tomato during postharvest storage. Postharvest Biology and Technology. 2006, 41: 151-155.
[5] Martínez-Valverde I, Periago M J, Provan G, et al. Phenolic compounds, lycopene and antioxidant activity in commercial varieties of tomato (Lycopersicum esculentum). Journal of the Science of Food and Agriculture. 2002, 82: 323-330.
[6] Ran F A, Patrick D H, Wright J, et al. Genome engineering using the CRISPR-Cas9 System. Nature Protocols, 2013, 8: 2281-2308
[7] Shalem O, Sanjana N E, Hartenian E, et al. Genome-scale CRISPR-Cas9 knockout screening in human cells. Science, 2014, 343:84-87.
[8] Srinivasan R, Babu S and Gothandam K M. Accumulation of Phytoene, a colorless carotenoid by inhibition of phytoene desaturase (PDS) gene in Dunaliella salina V-101. Bioresource Technology, 2017, 242: 311-318.
[9] PREDICTED: Solanum lycopersicum uncharacterized LOC101246275, mRNA GenBank: XM_004246695.4; Aug. 8, 2018.

The invention claimed is:

1. A method for increasing lycopene content in a tomato fruit comprising:
   1) inserting a nucleobase C in the first exon of Lycopene Increasing Effectively 1 (LIE) gene having the nucleotide sequence of SEQ ID NO:1, wherein the insertion results in a frameshift mutation in the LIE1 gene having the nucleotide sequence of SEQ ID NO:2; and/or
   2) deleting a nucleobase T in the second exon of the LIE1 gene, wherein the deletion results in a frameshift mutation in the LIE1 gene having the nucleotide sequence of SEQ ID NO:3.

2. The method of claim 1, wherein the method comprises:
   1) obtaining a gene specific targeting sgRNA having the following sequence:

```
   sgRNA-1:
                               (SEQ ID NO. 4)
   5'-TCTTCTCAATACATCCACA-3';
   or sgRNA-2:
                               (SEQ ID NO. 5)
   '5'-GGCTGAATATTTGCATGTT-3';
   ```

2) constructing a CRISPR/Cas9 vector using the sgRNA sequence obtained in step 1); and
   3) transforming the vector obtained in step 2) into a tomato to obtain a transgenic tomato plant.

3. A transgenic tomato plant comprising a frameshift mutation in Lycopene Increasing Effectively 1 (LIE) gene having the wild type nucleotide sequence of SEQ ID NO:1, wherein the frameshift mutation results in a mutant LIE1 gene having the nucleotide sequence of SEQ ID NO:2 or SEQ ID NO:3.

4. A transgenic tomato plant comprising a frameshift mutation in Lycopene Increasing Effectively 1 (LIE) gene having the nucleotide sequence of SEQ ID NO:1, wherein the frameshift mutation is made by a method comprising:
   1) inserting a nucleobase C in the first exon of the LIE1 gene, wherein the insertion results in a frameshift mutation in the LIE1 gene having the nucleotide sequence of SEQ ID NO:2; and/or
   2) deleting a nucleobase T in the second exon of the LIE1 gene, wherein the deletion results in a frameshift mutation in the LIE1 gene having the nucleotide sequence of SEQ ID NO:3 in the second exon of the LIE1 gene.

* * * * *

SEQUENCE LISTING

```
<160> NUMBER OF SEQ ID NOS: 21

<210> SEQ ID NO 1
<211> LENGTH: 312
<212> TYPE: DNA
<213> ORGANISM: Solanum lycopersicum

<400> SEQUENCE: 1
atgggtgatt cttcttctca atacatccac atggtgcaac acttgataga agaatgtata     60
atattcaata tgagccaaga agaatgcatg gatgctctat ccaaacatgc aaatattcag    120
cctattatca cttccacagt gtggaaggaa ttggagaaag aaaacaaaga gttctttgag    180
gcatacaaca agaaaacgag agaagcaaga agaccatcat caatacatga tgaattggag    240
atgtcaagac aaagaatcca ttgtataatg ttggattctt cctctaataa agactccaag    300
gaaaaacaat ag                                                        312

<210> SEQ ID NO 2
<211> LENGTH: 313
<212> TYPE: DNA
<213> ORGANISM: Artificial Sequence
<220> FEATURE:
<223> OTHER INFORMATION: Synthetic

<400> SEQUENCE: 2
atgggtgatt cttcttctca atacatccca catggtgcaa cacttgatag aagaatgtat     60
aatattcaat atgagccaag aagaatgcat ggatgctcta tccaaacatg caaatattca    120
gcctattatc acttccacag tgtggaagga attggagaaa gaaaacaaag agttctttga    180
ggcatacaac aagaaaacga gagaagcaag aagaccatca tcaatacatg atgaattgga    240
gatgtcaaga caaagaatcc attgtataat gttggattct tcctctaata aagactccaa    300
ggaaaaacaa tag                                                       313

<210> SEQ ID NO 3
<211> LENGTH: 311
```

<212> TYPE: DNA
<213> ORGANISM: Artificial Sequence
<220> FEATURE:
<223> OTHER INFORMATION: Synthetic

<400> SEQUENCE: 3
atgggtgatt cttcttctca atacatccac atggtgcaac acttgataga agaatgtata    60
atattcaata tgagccaaga agaatgcatg gatgctctat ccaaacagca aatattcagc   120
ctattatcac ttccacagtg tggaaggaat tggagaaaga aaacaaagag ttctttgagg   180
catacaacaa gaaaacgaga gaagcaagaa gaccatcatc aatacatgat gaattggaga   240
tgtcaagaca aagaatccat tgtataatgt tggattcttc ctctaataaa gactccaagg   300
aaaaacaata g                                                        311

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
tcttctcaat acatccaca                                                 19

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
ggctgaatat ttgcatgtt                                                 19

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tgattgtctt ctcaatacat ccaca                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
aaactgtgga tgtattgaga agaca                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
tgattgggct gaatatttgc atgtt                                          25

```
<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
aaacaacatg caaatattca gccca                                              25

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tcccagtcac gacgttgtaa                                                    20

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ttcaagttga taacggacta gc                                                 22

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
caattttatt ttgaacggag                                                    20

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
tttacctgtg gaagtgat                                                      18

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
acgaaacaga aatacttggc                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic
```

<400> SEQUENCE: 15
cttccgacaa cttcttttgg                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
cagcagatgt ggatctcaaa                    20

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17
ctgtggacaa tggaaggac                     19

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ttcttctcaa tacatccaca                    20

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
ttcttctcaa tacatcccaca                   21

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ccaaacatgc aaatattcag                    20

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
ccaaacagca aatattcag                     19